United States Patent [19]

Janusz et al.

[11] Patent Number: 4,544,668
[45] Date of Patent: Oct. 1, 1985

[54] COMPOUNDS AND COMPOSITIONS USEFUL FOR PRODUCING ANALGESIA

[75] Inventors: John M. Janusz, Fairfield, Ohio; Brian L. Buckwalter, Yardley, Pa.; Thomas R. LaHann, Cleves, Ohio

[73] Assignee: The Procter & Gamble Company, Cincinnati, Ohio

[21] Appl. No.: 514,205

[22] Filed: Jul. 14, 1983

[51] Int. Cl.$^4$ .................... A01N 37/02; A01N 37/06; A01N 37/18; A61K 31/165
[52] U.S. Cl. .................... 514/563; 260/404; 514/599; 514/613
[58] Field of Search .............. 260/404; 424/324, 311; 514/563, 599, 613

[56] References Cited

U.S. PATENT DOCUMENTS

| 3,268,582 | 8/1966 | Zeile et al. | |
| 3,558,500 | 1/1971 | Hollis et al. | 260/404 |
| 3,621,043 | 11/1971 | Seki et al. | 260/404 |
| 3,741,999 | 6/1973 | Seki et al. | 260/404 |
| 3,803,185 | 4/1974 | Henrick et al. | 260/404 |
| 3,816,484 | 6/1974 | Henrick | 260/404 |
| 3,888,893 | 6/1975 | Siddall | 260/404 |
| 3,897,428 | 7/1975 | Omura et al. | 260/404 |
| 3,920,523 | 11/1975 | Lichtenwalter et al. | 260/404 |
| 4,238,508 | 12/1980 | Nelson | |
| 4,313,958 | 2/1982 | LaHann | 424/324 |
| 4,401,663 | 8/1983 | Buckwalter et al. | 424/321 |

FOREIGN PATENT DOCUMENTS

| 626897 | 5/1963 | Belgium . |
| 1336388 | 8/1963 | France . |
| 61-39413 | 10/1981 | Japan . |
| 61-47752 | 11/1981 | Japan . |

OTHER PUBLICATIONS

Chemical Abstracts 72 55035g (1970).
Ferris et al., "New Approach to Insecticidal Paints", *Aust. Commonwealth Dept. Supply Def. Stand. Lab. Tech. Note* No. 89 (1966), (*Chem. Abs.* 67:22919s).
Kiernan, "A Study of Chemically Induced Acute Inflammation in the Skin of the Rat *Quart. J. Exp. Physiol.*, vol. 62, (1977), pp. 151–161.
Jansco et al., "Direct Evidence for Neurogenic Inflammation and its Prevention by Denervation and by Pretreatment with Capsaicin," *Br. J. Pharm. Chemother.*, vol. 3 (1967), pp. 138–151.
Arvier, et al., "Modification by Capsaicin and Compound 4/80 of Dye Leakage Induced by Irritants in the Rat," *Br. J. Pharm.*, vol. 59, (1977), pp. 61–68.
Yaksh et al., "Intrathecal Capsaicin Depletes Substance P in the Rat Spinal Cord and Produces Prolonged Thermal Analgesia," *Science*, vol. 260, (1979), pp. 481–483.
Virus et al., "Pharmacologic Actions of Capsaicin: Apparent Involvement of Substance P and Serotonin," *Life Sciences*, vol. 24, (1979), pp. 1273–1281.
Jones et al., "The Relation Between Chemical Constitution and Pungency in Acid Amides," *J. Chem. Soc.*, vol. 27, (1925), pp. 2588–2598.
Newman, "Natural and Synthetic Pepper-Flavored Substances," *Chem. Prod.*, (Mar. 1954), pp. 102–106.
Szolesanyi et al., "Sensory Effects of Capsaicin Congeners," *Arzneim.-Forsch.*, vol. 25, (1975), pp. 1871–1881.
Szolesanyi et al., "Sensory Effects of Capsaicin Congeners," *Arzneim.-Forsch.*, vol. 26, (1976), pp. 33–37.
Hegyes et al., "Synthesis of Homovanillic Acid Derivatives of Capsaicin-Like Effect," *Acta. Phys. Chem.*, vol. 20, (1974), pp. 115–120.
Michalski et al., "Synthesis and Local Anesthetic Properties of N-Substituted 3,4-Dimethoxyphenethylamine Derivatives," *Diss. Pharm. Pharmacol.*, vol. 24, (1972), pp. 17–25, (*Chem. Abs.* 77:19271a).
T. Szeki, "Contributions Towards Understanding the Relation Between the Chemical Constitution and the Sharp Taste of Acylamines," *Arch. Pharm.*, vol. 268, (1930), pp. 151–157.
Ott et al., *Liebigs Ann.* vol. 425 (1921), pp. 314–337.

*Primary Examiner*—Helen M. S. Sneed
*Attorney, Agent, or Firm*—David K. Dabbiere; Steven J. Goldstein; David L. Suter

[57] ABSTRACT

Methylenealkanamide compounds, and pharmaceutically-acceptable salts thereof, of the formula:

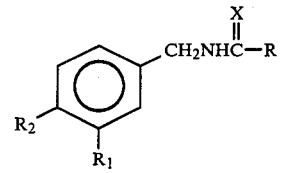

wherein X is O or S; R is straight or branched methylene substituted alkane having from 11 to 23 carbon atoms; $R_1$ is H, OH, or $OCH_3$; $R_2$ is OH or a short-chain ester; and wherein at least one of $R_1$ and $R_2$ is OH or $OCH_3$. Compositions, useful for producing analgesia in humans or lower animals, comprise a safe and effective amount of: a methylenealkanamide, pharmaceutically-acceptable salts thereof, or mixtures thereof; and a pharmaceutically-acceptable carrier. Preferably, these methylenealkanamides are N-vanillyl-methylenealkanamides. Methods of treatment, comprising administering a safe and effective amount of these methylenealkanamides, pharmaceutically-acceptable salts thereof, or mixtures thereof, include methods of parenteral, oral and topical administration.

15 Claims, No Drawings

COMPOUNDS AND COMPOSITIONS USEFUL FOR PRODUCING ANALGESIA

BACKGROUND OF THE INVENTION

This invention relates to compositions, containing certain methylene substituted-N-phenylmethylalkanamides, having analgesic activity.

While "pain" is incapable of precise definition due to its basically subjective nature, it can generally be said that the term refers to feelings of distress or suffering caused by stimulation of specialized nerve endings. A great variety of drugs have been developed to reduce pain in man and other animals; some directed to eliminating pain at its source, and others directed to blocking the assimilation of pain by the brain. Among the latter group of drugs that are designed to block the sensation of pain, are the analgesics, which generally relieve pain without causing unconsciousness. Analgesics can be further classified in two main categories: opioid analgesics, including morphine, codeine, levorphanol, and the morphine-like analgesics meperidine, and methadone; and antipyretic analgesics, such as aspirin, phenacetin, acetaminophen, phenylbutazone, and indomethacin.

Although the precise pharmacological action of these analgesics is uncertain, there are certain effects which readily distinguish the opioid analgesics from the antipyretics. In particular, the antipyretics are weak analgesics, with much of their effect in the peripheral nervous system, so that behavioral changes do not usually occur. Generally, these analgesics relieve only somatic pain originating from muscles, joints, tendons and fasciae, and are ineffective against deep visceral pain. However, the opioid analgesics are quite effective against all types of pain, with broad based action in the central nervous system. Aside from potent analgesia, the opioids, also known as narcotics, often produce effects on mood and other behavioral changes. Perhaps the most notable side effect of the opioid analgesics is the fact that their repeated use is associated with tolerance as well as psychic and physical dependence.

It has been recently discovered that capsaicin, a natural product of certain species of the genus Capsicum, induces analgesia in animals. Capsaicin (8-methyl-N-vanillyl-6E-nonenamide) and "synthetic" capsaicin (N-vanillylnonanamide) are disclosed as analgesics in U.S. Pat. No. 4,313,958, LaHann, issued Feb. 2, 1982. Analgesic activity of capsaicin has also been discussed in the chemical and medical literature, including Yaksh, et al., *Science*, 206, 481–483 (1979). The use of capsaicin to prevent dipilatory irritation is also disclosed in U.S. patent application Ser. No. 330,731, LaHann, et al., filed Dec. 14, 1981.

Specifically, capsaicin prevents the development of cutaneous hyperalgesia and also provides relief of deep visceral pain and severe pain. In certain tests, capsaicin produces a level of analgesia comparable to morphine, yet it is not antagonized by such narcotic antagonists as nalorphine and naloxone. Thus, capsaicin does not appear to belong to either of the major categories of analgesics, described above.

Compounds structurally similar to capsaicin have been described in the chemial literature. These references, though, do not suggest analgesic activity for these compounds. For example, Newman, "Natural and Synthetic Pepper-Flavored Substances (6)," *Chemical Products*, 102–106 (1954) lists the relative pungency of approximately 164 compounds, including N-vanilyloleamide and other alkenamide derivatives of capsaicin. Ott and Zimmermann, *Liebigs Ann.*, 425, 314–337 (1921) discloses a synthesis for N-vanillyloleamide. A synthesis for N-vanillyllinoleamide is disclosed in Ferris, *Australian Commonwealth, Dep. Supply, Def. Stand. Lab.*, No. 89 (1966) (Chem. Abs. 67:22919).

U.S. Pat. No. 4,238,505, Nelson, issued Dec. 9, 1980, discloses 3-hydroxyacetanilide for use in producing analgesia in animals. U.S. patent application Ser. No. 359,464, LaHann, et al., filed Mar. 18, 1982 now U.S. Pat. No. 4,424,206, issued Jan. 3, 1984, describes hydroxyphenylacetamides with analgesic and anti-irritant activity. Similarly, analgesic and anti-irritant activity is disclosed for N-vanillylsulfonamides in U.S. patent application Ser. No. 360,953, Buckwalter, et al., filed Mar. 23, 1982 now U.S. Pat. No. 4,401,663, issued Aug. 30, 1983; N-vanillylureas in U.S. patent application Ser. No. 381,672, Buckwalter, et al., filed May 25, 1982 now U.S. Pat. No. 4,460,602, issued July 17, 1984; and N-vanillylcarbamates in U.S. patent application Ser. No. 384,685, Buckwalter, et al., filed June 3, 1982 now U.S. Pat. No. 4,443,473, issued Apr. 17, 1983.

It has now been discovered that certain methylene substituted-N-phenylmethylalkanamides have analgesic activity in humans and lower animals. In particular, these alkanamides have potent analgesic activity similar to that of capsaicin, but are substantially less toxic.

SUMMARY OF THE INVENTION

The present invention provides compounds, useful for producing analgesia in humans and lower animals, of the formula:

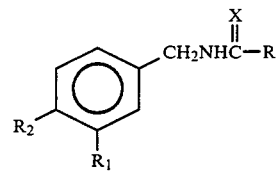

wherein X is O or S, R is straight or branched methylene substituted-alkane having from 11 to 23 carbon atoms, $R_1$ is H, OH, or $OCH_3$, $R_2$ is OH or a shortchain ester, and wherein at least one of $R_1$ and $R_2$ is OH or $OCH_3$; and pharmaceutically-acceptable salts thereof.

This invention also provides compositions comprising a safe and effective amount of these compounds, or mixtures thereof, and a pharmaceutically-acceptable carrier. Also provided are methods for producing analgesia by administering the compounds and compositions of this invention.

DESCRIPTION OF THE INVENTION

The compositions and methods of this invention incorporate certain methylene substituted-N-[(substituted phenyl)methyl]alkanamides (e.g., methylene substituted-N-vanillyl-alkanamides), or pharmaceutically-acceptable salts thereof, (herein "methylenealkanamides") of the formula:

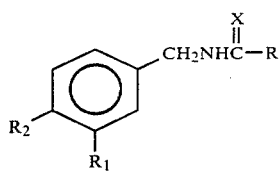

wherein X is O or S; R is straight or branched, methylene substituted alkane having from 11 to 23 carbon atoms; $R_1$ is H, OH or $OCH_3$; $R_2$ is OH or a short-chain ester; and wherein at least one of $R_1$ and $R_2$ is OH or $OCH_3$. R preferably contains from 16 to 21 carbon atoms and, preferably, the methylene substitution is at position six or greater, i.e., wherein R is a (n-methylenealkane), n is at least six. Also preferred are methylenealkanamides wherein X is O, methylenealkanamides wherein $R_1$ is $OCH_3$ and $R_2$ is OH, and methylenealkanamides wherein $R_2$ is a short-chain (i.e., $C_1$-$C_6$) ester, e.g., acetoxy.

A particularly preferred methylenealkanamide is 9-methylene-N-vanillyl-octadecanamide. Preferred pharmaceutically-acceptable salts include the sodium, potassium, calcium, magnesium, and ammonium salts.

Compositions

The compositions of the present invention comprise:
(a) a safe and effective amount of a methylenealkanamide; and
(b) a pharmaceutically-acceptable carrier.

A safe and effective amount of methylenealkanamide is that amount which provides analgesia, thereby alleviating or preventing the pain being treated at a reasonable benefit/risk ratio, as is intended with any medical treatment. Obviously, the amount of methylenealkanamide will vary with such factors as the particular condition that is being treated, the severity of the condition, the duration of the treatment, the physical condition of the patient, the nature of concurrent therapy (if any), the specific formulation and carrier employed, and the solubility and concentration of methylenealkanamide therein.

Depending upon the particular route of administration, a variety of pharmaceutically-acceptable carriers, well known in the art, may be used. These include solid or liquid fillers, diluents, hydrotropes, surface-active agents, and encapsulating substances. The amount of the carrier employed in conjunction with the methylenealkanamide is sufficient to provide a practical quantity of material per unit dose of analgesic.

Pharmaceutically-acceptable carriers for systemic administration, that may be incorporated into the compositions of this invention, include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Specific pharmaceutically-acceptable carriers are described in the following U.S. patent applications, all incorporated by reference herein: Ser. No. 359,464, LaHann, et al., filed Mar. 18, 1982 now U.S. Pat. No. 4,424,206, issued Jan. 3, 1984; Ser. No. 360,953, Buckwalter, et al., filed Mar. 23, 1982 now U.S. Pat. No. 4,401,663, issued Aug. 30, 1983; Ser. No. 381,672, Buckwalter, et al., filed May 25, 1982 now U.S. Pat. No. 4,460,602, issued July 17, 1984; and Ser. No. 384,685, Buckwalter, et al., filed June 3, 1982 now U.S. Pat. No. 4,443,473 issued Apr. 17, 1984. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50% of the methylenealkanamide. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules and effervescent preparations reconstituted from effervescent granules, containing suitable solvents, preservatives, emulsifying agents, suspending agents, diluents, sweeteners, melting agents, coloring, and flavoring agents. Preferred carriers for oral administration include gelatin, propylene glycol, cottonseed oil and sesame oil. Specific examples of pharmaceutically-acceptable carriers and excipients that may be used to formulate oral dosage forms, which may be used in formulating oral dosage forms containing methylenealkanamides, are described in U.S. Pat. No. 3,903,297, Robert, issued Sept. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated by reference herein.

The compositions of the present invention can also be administered topically to a biologic subject, i.e., by the direct laying on or spreading of the composition on epidermal or epithelial tissue. Such compositions include lotions, creams, solutions, gels and solids. These topical compositions comprise a safe and effective amount, usually at least about 0.5%, and preferably from about 1% to about 2%, of the methylenealkanamide. Suitable carriers for topical administration of the methylenealkanamide preferably remain in place on the skin as a continuous film and resist being washed off easily by perspiration or by immersion in water. Generally, the carrier is organic in nature and capable of having dispersed or dissolved therein the methylenealkanamide. The carrier may include pharmaceutically-acceptable emollients, emulsifiers, thickening agents, and solvents.

Specific systemic and topical formulations useful in this invention are described in the following U.S. patent applications, all incorporated by reference herein: Ser. No. 359,464, LaHann, et al., filed Mar. 18, 1982 now U.S. Pat. No. 4,424,206, issued Jan. 3, 1984; Ser. No. 360,953, Buckwalter, et al., filed Mar. 23, 1982 now U.S. Pat. No. 4,401,663, issued Aug. 30, 1983; Ser. No. 381,672, Buckwalter, et al., filed May 25, 1982 now U.S. Pat. No. 4,460,602, issued July 17, 1984; and Ser. No. 384,685, Buckwalter, et al., filed June 3, 1982 now U.S. Pat. No. 4,443,473, issued Apr. 17, 1984. Topical vehicles, useful herein, are disclosed in the following U.S. patent applications, incorporated by reference herein: "Improved Penetrating Topical Pharmaceutical Compositions Containing 1-dodecylazacycloheptan-2-one", Ser. No. 506,275, Cooper, filed June 21, 1983; and "Penetrating Topical Pharmaceutical Compositions Containing N-(2-hydroxyethyl)-pyrrolidone", Ser. No. 506,273, Cooper, filed June 21, 1983. Additional formulations, useful for parenteral, oral, and topical administration of methylenealkanamides, are disclosed in the following U.S. patent applications concurrently filed herewith, all incorporated by reference herein: "Compositions Useful for Producing Analgesia", Ser. No. 514,206, filed July 14, 1983 LaHann and Buckwalter; "Novel Compounds and Compositions Useful for Producing Analgesia", Ser. No. 514,207, filed July 14, 1983, LaHann, Janusz and Buckwalter; and "Novel Compounds and Compositions Useful for Producing Analgesia", Ser. No. 514,204, filed July 14, 1983 Janusz and LaHann.

Methods for Producing Analgesia

The present invention also encompasses methods of producing analgesia in humans or lower animals through administering, to the human or lower animal, a safe and effective amount, usually from about 1 mg to about 3600 mg per day, preferably from about 200 mg to about 2000 mg per day, of a methylenealkanamide. While dosages higher than the foregoing are effective to produce analgesia, care must be taken in some individuals to prevent adverse side effects. The methylenealkanamides and compositions of this invention can be used to treat and prevent pain, and to provide analgesia in various disorders at the deeper structures, muscles, tendons, bursa and joints associated with disease and trauma, and in various other conditions in which compounds such as aspirin, codeine, and morphine have heretofore been used to alleviate pain and discomfort.

The methylenealkanamides and compositions of the instant invention can be administered topically or systemically. Systemic application includes any method of introducing the methylenealkanamide into the tissues of the body, e.g., intrathecal, epidural, intramuscular, transdermal, intravenous, intraperitoneal, subcutaneous, sublingual, and oral administration.

A preferred method of parenteral administration is through intramuscular injection. As is known and practiced in the art, all formulations for parenteral administration must be sterile. For mammals, especially humans, (assuming an approximate body weight of 70 kg) individual doses of from about 2 mg to about 400 mg of methylenealkanamide are acceptable. Individual doses of from about 50 mg to about 200 mg are preferred.

A preferred method of systemic application of the methylenealkanamides is through oral administration. For mammals, especially humans, (assuming an approximate body weight of 70 kg) individual doses of from about 1 mg to about 900 mg of methylenealkanamide are acceptable. Individual doses of from about 50 mg to about 600 mg are especially preferred.

Topical administration can be used to produce local or systemic analgesia, through directly laying on or spreading a safe and effective amount of the methylenealkanamide, or composition containing a methylenealkanamide, on epidermal or epithelial tissue, including outer skin and oral, gingival, and nasal tissue. The amount of methylenealkanamide to be topically administered depends upon such factors as the sensitivity, type and location of tissue to be treated, the composition and carrier (if any) to be administered, and the particular methylenealkanamide to be administered as well as the particular disorder to be treated and the extent to which systemic (as distinguished from local) analgesic effects are desired. The extent of systemic analgesia also depends upon such factors as the amount of methylenealkanamide, the area of tissue to be covered, and the ability of the methylenealkanamide composition to penetrate the skin tissues.

The following non-limiting Examples illustrate the compositions, processes, and uses of the present invention.

EXAMPLE 1

9-methylene-N-vanillyl-octadecanamide was synthesized by the following method:

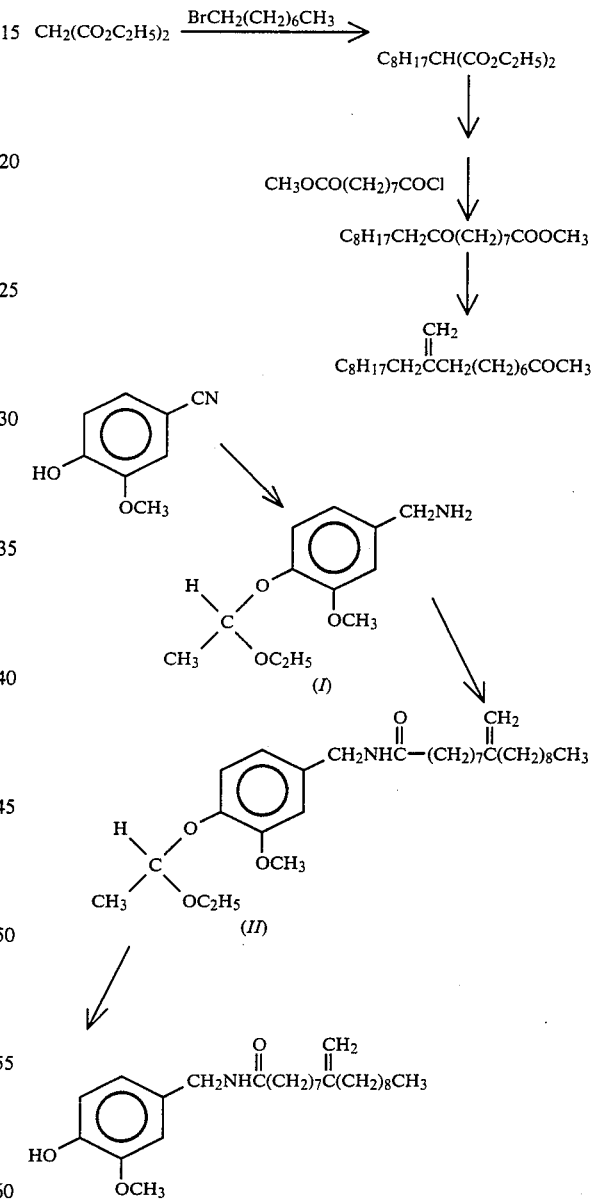

Specifically, 63 ml diethylmalonate were added to 150 ml of sodium ethoxide (prepared using ethanol and 8 g of sodium), warmed to 60° C., and stirred. Bromooctane (71 ml) was added, dropwise, the mixture warmed to 75°–80° C., and stirred for overnight. The ethanol was evaporated, the mixture taken up in ethyl ether and water, the layers separated, the ether layer washed with water and brine, then dried to yield 105 g of $C_8H_{17}CH(CO_2C_2H_5)_2$. This product was distilled, collecting 56.8 g, and then added dropwise to 200 ml of a solution of potassium hydroxide (75 g) in ethanol, which was refluxed overnight. The solution was cooled and ethanol evaporated. The residue was dissolved in 500 ml $H_2O$ and acidified with HCl. The product was extracted with ether and ether phase was washed with water and brine, and then dried and filtered, yielding 43 g of $C_8H_{17}CH(CO_2H)_2$.

In a separate process, 23.9 g of azelaic monomethylester was dissolved in 30 ml chloroform. Oxalylchloride (15 ml) was added, all at once, and the mixture refluxed 2 hours at 50° C. The mixture was cooled; excess solvent and oxalylchloride were evaporated. After distillation, 25.8 g of $CH_3OCO(CH_2)_7COCl$ was obtained.

3 grams of the $C_8H_{17}CH(CO_2H)_2$ product obtained above were added, in small portions, to a mixture of 3.3 ml dihydropyran in 25 ml of benzene and 20 μl sulfuric acid, and stirred at 25° C., for 1 hour. Potassium hydroxide was added to neutralize the sulfuric acid, and the mixture was stirred for an additional 30 minutes. The solvent was then evaporated and, with 25 ml benzene, the mixture was added dropwise to NaH in 30 ml benzene, and stirred for 1 hour. 3 g of the $CH_3OCO(CH_2)_7COCl$ product prepared above was added dropwise and the mixture stirred overnight. Acetic acid (0.3 ml) was added and the mixture refluxed for 4 hours. The residue was taken up in ether, washed with 1N NaOH, water and brine, and dried. Chromatography on silica gel with 15% ethylacetate and hexane gave 1.5 g of $C_8H_{17}CH_2CO(CH_2)_7COOCH_3$.

A round bottom flask was cleaned, dried, charged with 3.6 ml of 50% NaH, and cleared with pentane washes. The flask was then purged with argon and 75 ml of distilled dimethyl sulfoxide (DMSO) added via syringe, and heated to 70° C. for 45 minutes. After hydrogen evolution had stopped, the solution was cooled in a water bath and 26.8 g methyltriphenylphosphonium bromide, in 100 ml DMSO, was added all at once to the reaction solution and stirred for 20 minutes at room temperature. 18 g of $C_8H_{17}CH_2CO(CH_2)_7COOCH_3$, prepared as above, was dissolved in 50 ml DMSO, added all at once to the reaction solution, and stirred overnight. The mixture was then poured into 250 ml water and extracted twice with 50/50 toluene and pentane. The organic phase was washed with water, dried and evaporated. The residue was filtered through silica gel to give 16.7 g of $C_8H_{17}CH_2C(CH_2)CH_2(CH_2)_6COOCH_3$. This product was dissolved in 150 ml ethanol, and 3 g potassium hydroxide in 15 ml water was added gradually with stirring. The mixture was refluxed for 3 hours. The solvent was evaporated and residue taken up in 150 ml of 0.1N NaOH, transferred to separatory funnel with 100 ml water, and extracted with ether, taking care not to shake vigorously. The aqueous phase was acidified with HCl and extracted with ether. The combined extracts were washed with water and brine, and then dried, yielding 14.3 g of $C_8H_{17}CH_2C(CH_2)CH_2(CH_2)_6CO_2H$.

In a separate procedure, 20 g of 4-hydroxy-3-methoxybenzonitrile was mixed with 50.7 ml ethylvinyl ether, stirred, and chilled in an ice bath. Sufficient tetrahydrofuran (THF) was added to dissolve the nitrile. Trifluoroacetic acid (2 ml) was added dropwise and the mixture allowed to stir overnight at room temperature. 7.5 ml of triethylamine was added and stirred briefly. The solvent was then evaporated, the residue taken up in ethyl ether and washed with NaOH, water and brine, and dried to give 31 g of protected product. 3.5 g of this product, dissolved in THF, was added dropwise at 0° C. to a flask containing 50 ml THF and 3 g $LiAlH_4$. The mixture was stirred at room temperature for 3 hours, quenched with wet $Na_2SO_4$, filtered, and the solvent evaporated yielding 3 g of Product (I) depicted in the schematic above.

2.2 g of Product (I) and 3.1 g of the $C_8H_{17}CH_2C(CH_2)CH_2(CH_2)_6CO_2H$ product, prepared above, were dissolved together in 25 ml dry methylene chloride, and chilled to 0° C. in an ice bath. N,N-dicyclohexylcarbodiimide (2.1 g) was dissolved in methylenechloride and added to the reaction mixture. The mixture was placed under argon and stirred overnight. The resulting solids were filtered and rinsed with methylene chloride. The filtrate was transferred to a separatory funnel, washed with HCl, $Na_2CO_3$ and water, then dried, yielding 6.3 g of Product (II), depicted above. This product was dissolved in 50 ml THF, 10.4 1N HCl were added all at once, and the mixture was stirred at room temperature for 45 minutes. The THF was evaporated, the residue partitioned between water and ethyl ether, and the aqueous phase was extracted with ether. The ether phase was extracted with 1N NaOH, the layers separated, and the aqueous phase acidified with HCl. The product was extracted into ether and the extracts were washed with water and brine, and dried, yielding 4 grams of 9-methylene-N-vanillyl-octadecanamide. Purification by silica gel chromatography with 50% ethyl acetate and hexane gave 3.4 g of analytically pure product. Its structure was confirmed via nuclear magnetic resonance and infrared spectroscopy.

In the example above, other methylenealkanamides are made by replacing azelaic monomethyl ester and bromooctane, so as to vary placement of the methylene substitution and the number of carbon atoms in the R group of the methylenealkanamide. For example, 9-methylene-N-vanillyl-hexadecanamide and 9-methylene-N-vanillyl-eicosenamide are made by replacing bromooctane with bromohexane and bromodecane, respectively, in the above synthesis. Also, for example, 8-methylene-N-vanillyl-heptadecanamide and 4-methylene-N-vanillyl-tridecanamide are made by replacing azelaic monomethyl ester with suberic monomethyl ester and succinic monomethyl ester, respectively, in the above synthesis.

EXAMPLE II

An analgesic composition, according to the present invention, was made comprising:

| | |
|---|---|
| 9-methylene-N—vanillyl-octadecanamide | 132.4 mg |
| ethanol | 0.75 ml |
| pyrrolidone | 0.75 ml |

The composition was made by simple dissolution of the methylenealkanamide in the liquid solvents. A mouse weighing 30 g, was injected subcutaneously with 0.1 ml of the composition, producing analgesia.

In the above example, 9-methylene-N-vanillyl-hexadecanamide, 9-methylene-N-vanillyl-eicosanamide, 8-methylene-N-vanillyl-heptadecanamide, and 4-methylene-N-vanillyl-tridecanamide are substituted, respectively, for 9-methylene-N-vanillyl-octadecanamide, with substantially similar results.

EXAMPLE III

A composition, according to the instant invention, for parenteral administration, is made with the following ingredients:

| 9-methylene-N—vanillyl-octadecanamide | 100 mg/ml of carrier |
|---|---|
| carrier (percent-by-weight): | |
| propylene glycol | 72% |
| polyethylene glycol | 17% |
| water | 10% |
| benzyl alcohol | 1% |

The methylenealkanamide is dissolved in the carrier and a human subject, weighing 70 kg, is injected subcutaneously with 1.0 ml of the composition thereby prepared, producing analgesia. At eight-hour intervals, two more subcutaneous injections are made, of 1.0 ml of the composition per administration, for a total of 300 mg 9-methylene-N-vanillyl-octadecanamide administered over a twenty-four hour period.

EXAMPLE IV

A composition, according to the instant invention, for parenteral administration, is made with the following components:

| 8-methylene-N—vanillyl-heptadecanamide | 100 mg/ml of carrier |
|---|---|
| carrier (percent-by-weight): | |
| sesame oil | 98% |
| benzyl alcohol | 2% |

A human subject, weighing 70 kg, is injected via deep-intramuscular injection, with 1.0 ml of the composition prepared above, producing analgesia.

EXAMPLE V

A composition, according to the instant invention, for parenteral administration, is made by admixing the following components:

| 9-methylene-N—[(4-acetoxy-3-methoxyphenyl)-methyl]-octadecanamide | 100 mg/ml of carrier |
|---|---|
| carrier (percent by weight): | |
| ethyl oleate | 98.0% |
| benzyl alcohol | 2.0% |

A human subject, weighing 70 kg, is injected via intramuscular injection, with 2.0 ml of the composition prepared above, producing analgesia.

EXAMPLE VI

A composition, according to the instant invention, for oral administration, is made with the following components:

| 9-methylene-N—vanillyl-octadecanamide | 100 mg/ml of carrier |
|---|---|
| carrier (percent-by-weight): | 100% |
| propylene glycol | |

5.0 ml of the syrup thereby prepared is administered orally to a human subject, producing analgesia.

In the above example, flavoring agents, sweetening agents such as sucrose, lactose, mannitol and saccharin, and preservatives such as glycerin, methyl paraben, propylparaben, benzoic acid, sodium benzoate and alcohol, are added, singly or in combination, to the composition formed above, with substantially similar results.

EXAMPLE VII

A composition, according to the instant invention, for oral administration, is made with the following components:

| Component | Bulk | Individual Tablet |
|---|---|---|
| 9-methylene-N—vanillyl-octadecanamide | 70 g | 350 mg |
| starch | 6 | 30 |
| magnesium stearate | 1 | 5 |
| microcrystalline cellulose | 20 | 100 |
| colloidal silicon dioxide | 0.5 | 2.5 |
| povidone | 2.5 | 12.5 |

The above ingredients are admixed into a bulk mixture, totalling 100 g. Compressed tablets are formed, using tabletting methods known in the art, each containing 0.5 g of the bulk mixture. A human subject, weighing approximately 70 kg, is orally administered two of the tablets, for a total dose of 700 mg of methylenealkanamide, producing analgesia.

EXAMPLE VIII

A composition, according to the instant invention, for oral administration, is made with the following components:

| 4-methylene-N—vanillyl-tridecanamide | 1000 mg |
|---|---|
| starch | 10.2 |
| magnesium stearate | 5.1 |

A capsule is made by filling with the above ingredients, and administered to a human subject, weighing approximately 70 kg, producing analgesia.

EXAMPLE IX

An ointment composition, according to the instant invention, for topical administration, is formed with the following components (percentages-by-weight):

| 9-methylene-N—vanillyl-octadecanamide | 2.0% |
|---|---|
| oleyl alcohol | 30.0% |
| cetyl alcohol | 40.0% |
| propylene glycol | 28.0% |

The components are admixed and approximately 6 ml of the ointment is applied to a 100 cm² portion of the skin of a human subject, producing analgesia.

What is claimed is:

1. Methylenealkanamide compounds, and pharmaceutically-acceptable salts thereof, of the formula:

$$\text{Ar}(R_1, R_2)\text{—CH}_2\text{NHC}(=X)\text{—R}$$

wherein X is O or S; R is straight or branched, methylene-substituted alkane having from 11 to 23 carbon atoms; R₁ is H, OH or OCH₃; R₂ is OH, or a short-chain ester; and wherein at least one of R₁ and R₂ is OH or OCH₃.

2. Methylenealkanamide compounds, and pharmaceutically-acceptable salts thereof, according to claim 1, wherein R₁ is OCH₃ and R₂ is OH.

3. Methylenealkanamide compounds, and pharmaceutically-acceptable salts thereof, according to claim 1, wherein R₂ is a short-chain ester.

4. Methylenealkanamide compound, and pharmaceutically acceptable salts thereof, according to claim 2, wherein said methylenealkanamide is 9-methylene-N-vanillyl-octadecanamide.

5. A composition for producing analgesia in humans or lower animals, comprising:
    (a) a safe and effective amount of a methylenealkanamide compound or pharmaceutically-acceptable salt thereof, or mixtures thereof, of the formula:

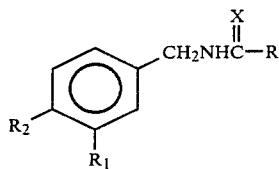

wherein X is O or S, R is straight or branched, methylene-substituted alkane having from 11 to 23 carbon atoms, R₁ is H, OH, or OCH₃, R₂ is OH or a chort-chain ester, and wherein at least one of R₁ and R₂ is OH or OCH₃; and
    (b) a pharmaceutically-acceptable carrier.

6. A composition, according to claim 5, wherein R is straight or branched, methylene-substituted alkane having from 16 to 21 carbon atoms.

7. A composition, according to claim 5, wherein R₁ is OCH₃ and R₂ is OH.

8. A composition, according to claim 5, wherein R₂ is a short-chain ester.

9. A composition, according to claim 5, comprising a pharmaceutically-acceptable salt of said methylenealkanamide compound, selected from the group consisting of sodium, potassium, calcium, magnesium, and ammonium salts.

10. A composition, according to claim 6, for parenteral administration, comprising at least about 90%, by weight, of said pharmaceutically-acceptable carrier.

11. A composition, according to claim 6, for oral administration, comprising from aout 25% to about 50%, by weight, of said methylenealkanamide.

12. A composition, according to claim 7, for producing analgesia in humans or lower animals, wherein said methylenealkanamide is 9-methylene-N-vanillyl-octadecanamide.

13. A composition, according to claim 8, wherein said methylenealkanamide is 9-methylene-N-[(4-acetoxy-3-methoxyphenyl)methyl]octadecanamide.

14. A method for producing analgesia in humans or lower animals, which comprises administering to said human or lower animal a safe and effective amount of a methylenealkanamide compound or pharmaceutically-acceptable salt thereof, or mixtures thereof, of the formula:

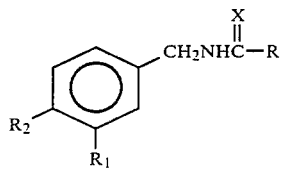

wherein X is O or S; R is straight or branched, methylene-substituted alkane having from 11 to 23 carbon atoms; R₁ is H, OH, or OCH₃; R₂ is OH or a short-chain ester; and wherein at least one of R₁ and R₂ is OH or OCH₃.

15. A method, according to claim 14, wherein R of said methylenealkanamide compound is straight or branched, methylene-substituted alkane having from 16 to 21 carbon atoms.

* * * * *